United States Patent
Kim et al.

(10) Patent No.: US 11,827,767 B2
(45) Date of Patent: Nov. 28, 2023

(54) PLASTICIZER COMPOSITION COMPRISING CYCLOHEXANE POLYESTER-BASED SUBSTANCE AND RESIN COMPOSITION COMPRISING THE SAME

(71) Applicant: LG CHEM, LTD., Seoul (KR)

(72) Inventors: Hyun Kyu Kim, Daejeon (KR); Jeong Ju Moon, Daejeon (KR); Woo Hyuk Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/772,065

(22) PCT Filed: Jul. 3, 2019

(86) PCT No.: PCT/KR2019/008139
§ 371 (c)(1),
(2) Date: Jun. 11, 2020

(87) PCT Pub. No.: WO2020/013515
PCT Pub. Date: Jan. 16, 2020

(65) Prior Publication Data
US 2021/0070965 A1 Mar. 11, 2021

(30) Foreign Application Priority Data

Jul. 12, 2018 (KR) .................. 10-2018-0081209

(51) Int. Cl.
*C08K 5/12* (2006.01)
*C08K 5/00* (2006.01)
*C08L 101/00* (2006.01)

(52) U.S. Cl.
CPC .............. *C08K 5/12* (2013.01); *C08K 5/0016* (2013.01); *C08L 101/00* (2013.01)

(58) Field of Classification Search
CPC ........ C08K 5/0016; C08K 5/12; C08K 5/101; C08K 13/00; C08K 2201/014; C08L 101/00; C08L 27/06; C08L 25/00; C08L 75/04; C08L 7/00; C08L 29/12; C08L 61/02; C08L 23/12; C08L 23/06; C08L 23/0853; C08L 31/04
See application file for complete search history.

(56) References Cited

U.S. PATENT DOCUMENTS

| T864,003 | I4 | 7/1969 | Foster | |
|---|---|---|---|---|
| 7,208,545 | B1 | 4/2007 | Brunner et al. | |
| 8,729,289 | B2* | 5/2014 | De Munck | C08K 5/10 |
| | | | | 560/1 |
| 10,633,511 | B2 | 4/2020 | Kim et al. | |
| 2005/0020718 | A1 | 1/2005 | Gosse et al. | |
| 2005/0101800 | A1 | 5/2005 | Büschken et al. | |
| 2006/0183936 | A1 | 8/2006 | Grass et al. | |
| 2007/0027244 | A1* | 2/2007 | Schar | C08K 5/521 |
| | | | | 524/284 |
| 2007/0293646 | A1* | 12/2007 | Gosse | C08K 5/0016 |
| | | | | 526/344 |
| 2009/0291304 | A1 | 11/2009 | Gosse et al. | |
| 2010/0108940 | A1 | 5/2010 | De Munck et al. | |
| 2010/0298477 | A1* | 11/2010 | Godwin | C08L 27/06 |
| | | | | 524/285 |
| 2010/0305250 | A1* | 12/2010 | Colle | C08K 5/0016 |
| | | | | 524/112 |
| 2010/0310891 | A1 | 12/2010 | Godwin | |

(Continued)

FOREIGN PATENT DOCUMENTS

| CN | 1592733 A | 3/2005 |
|---|---|---|
| CN | 101878259 A | 11/2010 |

(Continued)

OTHER PUBLICATIONS

Extended European Search Report issued by the European Patent Office dated Feb. 5, 2021 in corresponding European patent application No. 19833610.9.

(Continued)

*Primary Examiner* — Jane L Stanley
(74) *Attorney, Agent, or Firm* — Morgan, Lewis & Bockius LLP

(57) ABSTRACT

Provided is a plasticizer composition comprising a cyclohexane polyester-based substance which is a compound of Chemical Formula 1 as a plasticizer:

[Chemical Formula 1]

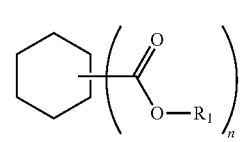

in combination with a perhydride comprising a compound of Chemical Formula 2 having a smaller number of ester groups than the cyclohexane polyester-based substance:

[Chemical Formula 2]

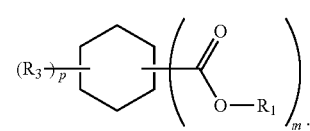

Also provided are resin compositions containing the plasticizer composition and methods of preparing the plasticizer composition.

16 Claims, No Drawings

(56) References Cited

U.S. PATENT DOCUMENTS

| | | | |
|---|---|---|---|
| 2015/0246867 A1 | 9/2015 | Castiglioni et al. | |
| 2016/0017126 A1* | 1/2016 | Mitamura | C08K 5/524 |
| | | | 524/147 |
| 2017/0088691 A1 | 3/2017 | Woldt et al. | |
| 2018/0105673 A1 | 4/2018 | Schilling, III et al. | |
| 2018/0163018 A1 | 6/2018 | Kim et al. | |
| 2018/0163019 A1 | 6/2018 | Kim et al. | |
| 2021/0163667 A1* | 6/2021 | Kramer | C08L 101/10 |
| 2022/0017721 A1* | 1/2022 | Uno | C08K 5/524 |
| 2023/0272171 A1* | 8/2023 | Villeneuve | C07D 251/32 |
| | | | 523/351 |

FOREIGN PATENT DOCUMENTS

| | | |
|---|---|---|
| CN | 107849299 A | 3/2018 |
| CN | 108779058 A | 11/2018 |
| DE | 20021356 U1 | 2/2001 |
| DE | 10146847 A1 | 4/2003 |
| EP | 2810982 A1 | 12/2014 |
| EP | 3214067 A1 | 9/2017 |
| EP | 3287484 A1 | 2/2018 |
| EP | 3293172 A2 | 3/2018 |
| JP | 2008-239582 A | 10/2008 |
| JP | 2015-217608 A | 12/2015 |
| KR | 10-2011-0093929 A | 8/2011 |
| KR | 10-2016-0047221 A | 5/2016 |
| KR | 10-2017-0121060 A | 11/2017 |
| KR | 10-2018-0022680 A | 3/2018 |
| WO | 00/78704 A1 | 12/2000 |
| WO | 03/103830 A1 | 12/2003 |
| WO | 2014/053535 A2 | 4/2014 |

OTHER PUBLICATIONS

Opposition to corresponding European Patent Application No. 19833610.9 filed in the European Patent Office dated Jun. 30, 2022.
Lacerda et al., "TiO2 Decorated Sand Grains for Photodegradation of Pollutants: Methylene Blue and Ciprofloxacin Study," Journal of the Brazilian Chemical Society, 2020, vol. 31, No. 1, pp. 201-210.
R&D Report, "Short report on the simulation of tests according to WO 00/78704A1".
R&D Report. "Short report on the simulation of tests according to WO 03/103830A1".

\* cited by examiner

PLASTICIZER COMPOSITION COMPRISING CYCLOHEXANE POLYESTER-BASED SUBSTANCE AND RESIN COMPOSITION COMPRISING THE SAME

CROSS-REFERENCE TO RELATED APPLICATIONS

This application is a National Stage Application of International Application No. PCT/KR2019/008139 filed on Jul. 3, 2019, which claims priority to and the benefit of Korean Patent Application No. 10-2018-0081209, filed on Jul. 12, 2018, the disclosures of which are incorporated herein by reference in their entirety.

TECHNICAL FIELD

The present invention relates to a plasticizer composition including a cyclohexane polyester-based substance in combination with a specific type of a perhydride, and a resin composition including the same.

BACKGROUND ART

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, adipate-, and other polymer-based plasticizers.

Meanwhile, there is an increasing demand for environment-friendly products in the plastisol industry relating to flooring materials, wallpaper, soft and hard sheets, and the like, the calendering industry, and the extruding/injecting compound industry, and in order to reinforce a quality feature, processability, and productivity of each finished product for such environment-friendly products, suitable plasticizers need to be used in consideration of discoloration, migration, mechanical properties, and the like.

Depending on properties required by industry in various areas of use, such as tensile strength, an elongation rate, light resistance, migration, gelability, an absorption rate, and the like, a PVC resin is mixed with a supplementary material such as a plasticizer, a filler, a stabilizer, a viscosity depressant, a dispersant, an antifoaming agent, a foaming agent, or the like.

By way of one example, among plasticizer compositions applicable to PVC, the use of di(2-ethylhexyl) terephthalate (DEHTP) that has a relatively low price and is most commonly used results in high hardness or high sol viscosity, a relatively low absorption rate of the plasticizer, poor migration, and poor migration upon stress.

To improve these properties, di(2-ethylhexyl) cyclohexane 1,4-diester (1,4-DEHCH) obtained by hydrogenating DEHTP can be considered. The 1,4-DEHCH can improve plasticization efficiency, whereas it exhibits poor migration, low thermal stability, and slightly degraded mechanical properties, and thus an improvement in several properties is required. However, there is currently no solution other than a method of mixing with other secondary plasticizers to overcome these problems.

Furthermore, the above-mentioned problems of 1,4-DEHCH obtained by hydrogenating DEHTP are also exhibited in DEHIP and 1,3-DEHCH as well as in trimellitate-based substances. In addition, in the case in which a terephthalate-based (or isophthalate-based or trimellitate-based) plasticizer is commercialized by means of hydrogenation, hydrogenation of lower-alcohol-derived terephthalate-based substances with slightly poor migration causes migration to worsen, and hydrogenation of higher-alcohol-derived terephthalate-based substances with a slightly low elongation rate causes an increase in cost only without improving an elongation rate. Therefore, the use of an alcohol in the case of a dicarboxylic acid-based hydrogenated substance is limited such that an alcohol has 8 or 9 carbon atoms.

In this circumstance, when the hydrogenation and the number of carbon atoms result in an improvement in migration, thermal stability, and mechanical properties of the hydrogenated substance, there are advantages such as cost reduction caused by simplification of a product and no need to carry out a blending process, prevention of degradation of plasticization efficiency caused by mixing, an increase in cost competitiveness and ease in supply of raw materials caused by using alcohols having various numbers of carbon atoms, and the like. Therefore, demand for development of the single plasticizer is continuing. In addition, since a plasticizer that can be used alone exhibits superior effects even when used in combination with other plasticizers, development of this plasticizer is continuously required.

DISCLOSURE

Technical Problem

The present invention is directed to providing a plasticizer composition capable of improving the above-described problems in terms of volatile loss, thermal stability, and mechanical properties such as an elongation rate and tensile strength by using cyclohexane polyester as a plasticizer in combination with a specific amount or less of a perhydride. Furthermore, the present invention is also directed to providing a method of preparing a plasticizer composition that is expected to improve cost competitiveness by simplifying a purification process.

Technical Solution

One aspect of the present invention provides a plasticizer composition including: a cyclohexane polyester-based substance which is a compound of the following Chemical Formula 1; and a perhydride comprising a compound of the following Chemical Formula 2, wherein the perhydride is included in an amount from 0.1 to 10 parts by weight with respect to 100 parts by weight of the cyclohexane polyester-based substance:

[Chemical Formula 1]

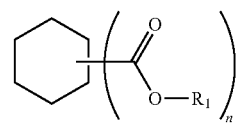

[Chemical Formula 2]

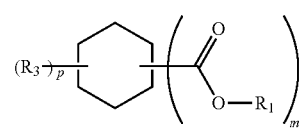

wherein in Chemical Formulas 1 and 2, $R_1$ and $R_2$ are each independently a C4 to C10 alkyl group, $R_3$ is a methyl group, n is 2 or 3, m is an integer from 0 to 2, p is an integer from 0 to 3, m+p is an integer from 0 to 3, and n−m is an integer from 1 to 3.

Another aspect of the present invention provides a resin composition including: a resin in an amount of 100 parts by weight; and the above-described plasticizer composition in an amount of 5 to 150 parts by weight.

The resin can be one or more selected from the group consisting of ethylene-vinyl acetate, polyethylene, polypropylene, polyketone, polyvinyl chloride, polystyrene, polyurethane, synthetic rubber, natural rubber, and a thermoplastic elastomer.

Advantageous Effects

A plasticizer composition according to an embodiment of the present invention can ensure environmental friendliness and improve mechanical properties such as tensile strength and an elongation rate and other properties such as volatile loss and the like to levels comparable or superior to those of existing products when used in a resin composition. In addition, the plasticizer composition can also be expected to improve thermal stability, and furthermore, cost competitiveness can be significantly enhanced by simplifying the preparation process.

Modes of the Invention

Terms and words used in this specification and claims should not be interpreted as being limited to commonly used meanings or meanings in dictionaries, and, based on the principle that the inventors can appropriately define concepts of terms in order to describe their invention in the best way, the terms and words should be interpreted with meanings and concepts which are consistent with the technological spirit of the present invention.

Definition of Terms

As used herein, the term "composition" encompasses a mixture of materials including the composition as well as reaction products and decomposition products formed from materials of the composition.

As used herein, the term "polymer" refers to a polymeric compound prepared by polymerizing homogeneous or heterogeneous monomers. Therefore, the generic term polymer encompasses a homopolymer commonly used to refer to a polymer prepared from only one type of a monomer and an interpolymer as defined below.

As used herein, the term "interpolymer" refers to a polymer prepared by polymerizing at least two types of different monomers. Therefore, the generic term interpolymer encompasses a copolymer commonly used to refer to a polymer prepared from two types of different monomers and a polymer prepared from two or more types of different monomers.

As used herein, the prefix "iso-" is used generically to mean an alkyl group such as a methyl group or an ethyl group is attached as a branched chain to the main chain thereof. In this specification, the prefix "iso-" can be used generically to mean an alkyl group such as a methyl group or an ethyl group is attached as a branched chain to the main chain thereof, including those bonded at the termini of the main chain, unless separately specified otherwise.

As used herein, the term "cyclohexane polyester-based substance" refers to a substance in which at least two ester groups are bonded to a cyclohexane ring, and the term "aromatic polyester-based substance" refers to a substance in which at least two ester groups are bonded to an aromatic ring, for example, to a ring of aromatic compounds such as benzene and the like, and is not a polymer "polyester". That is, the cyclohexane polyester-based substance refers to a substance in which at least two ester groups, for example, 3 to 6 ester groups are bonded to a cyclohexane ring, and in particular, a "cyclohexane diester-based substance" can be refer to a substance in which two ester groups are bonded to a cyclohexane ring.

As used herein, the term "cyclohexanepolycarboxylic acid" refers to a substance in which at least two carboxyl groups are bonded to a cyclohexane ring, and the term "aromatic polycarboxylic acid" refers a substance in which at least two carboxyl groups are bonded to an aromatic ring, for example, to a ring of benzene and the like.

As used herein, the term "straight vinyl chloride polymer" is one kind of vinyl chloride polymer that can be polymerized through suspension polymerization, bulk polymerization, or the like, and refers to a polymer which is in the form of a porous particle in which a large amount of pores with a size of several tens to several hundreds of micrometers are distributed and has no cohesion and excellent flowability.

As used herein, the term "paste vinyl chloride polymer" is one kind of vinyl chloride polymer that can be polymerized through microsuspension polymerization, seeded emulsion polymerization, pure emulsion polymerization, or the like, and refers to a polymer which is in the form of a fine, compact, and non-porous particle with a size of several tens to several thousands of nanometers and has cohesion and poor flowability.

The terms "comprising", "including", "having", and derivatives thereof are not intended to exclude the presence of any additional components, steps, or procedures, whether they are specifically disclosed or not. To avoid any uncertainty, all compositions claimed through the use of the terms "comprising" and "including", whether polymers or otherwise, can include any additional additives, adjuvants, or compounds unless otherwise stated. In contrast, the term "consisting essentially of" excludes any other component, step, or procedure from the scope of any subsequent description, and excludes those that are not essential to operability. The terms "consisting of" excludes any element, step, or procedure that is not specifically described or listed.

Measurement Methods

In the specification, the contents of components in the composition are analyzed through gas chromatography analysis using a gas chromatography instrument (Agilent 7890 GC manufactured by Agilent Technologies Inc., column: HP-5, carrier gas: helium (flow rate 2.4 mL/min), detector: F.I.D, injection volume: 1 μL, initial value: 70° C./4.2 min, terminal value: 280° C./7.8 min, program rate: 15° C./min).

In the specification, "hardness" refers to Shore hardness (Shore "A" and/or Shore "D") as measured at 25° C. in accordance with ASTM D2240. Hardness is measured using a 3T specimen for 10 seconds and can be an index for evaluating plasticization efficiency, and low hardness indicates excellent plasticization efficiency.

In the specification, "tensile strength" is measured in accordance with ASTM D638 as follows. A 1T specimen is pulled at a cross head speed of 200 mm/min using a universal testing machine (UTM; 4466 manufactured by Instron), a time point at which the specimen is broken is then determined, and a load applied at the time point is substituted into the following Equation 1.

Tensile strength (kgf/cm$^2$)=Applied load (kgf)/Thickness (cm)×Width (cm) [Equation 1]

In the specification, an "elongation rate" is measured in accordance with ASTM D638 as follows. A 1T specimen is pulled at a cross head speed of 200 mm/min using the UTM, a time point at which the specimen is broken is then determined, and a length at the time point is substituted into the following Equation 2.

Elongation rate (%)=Length after elongation/Initial length×100 [Equation 2]

In the specification, "migration loss" is measured in accordance with KSM-3156 as follows. A specimen with a thickness of 2 mm or more is prepared, glass plates are attached to both sides of the specimen, and a load of 1 kgf/cm² is then applied. Subsequently, the specimen is placed in a hot-air convection oven (80° C.) for 72 hours, then taken out of the oven, and cooled at room temperature for 4 hours. Afterward, the glass plates attached to both sides of the specimen are removed, weights of the specimen before being placed in and after taken out of the oven along with the glass plate were measured, and the resultant weights are substituted into the following Equation 3.

Migration loss (%)={(Initial weight of specimen at room temperature−Weight of specimen after being taken out of oven)/Initial weight of specimen at room temperature}×100 [Equation 3]

In the specification, "volatile loss" is measured by processing a specimen at 80° C. for 72 hours and then weighing the specimen.

Volatile loss (wt %)={(Initial weight of specimen−Weight of specimen after being processed)/Initial weight of specimen}×100 [Equation 4]

In the specification, an "absorption rate" is evaluated by measuring the time taken for the torque of a mixer to be stabilized during mixing of a resin and a plasticizer using a planetary mixer (Brabender, P600) at 77° C. and 60 rpm.

Hereinafter, the present invention will be described in more detail to facilitate understanding of the present invention.

Plasticizer Composition

A plasticizer composition according to an embodiment of the present invention includes: a cyclohexane polyester-based substance which is a compound of the following Chemical Formula 1; and a perhydride including a compound of the following Chemical Formula 2, wherein the perhydride is included in an amount from 0.1 to 10 parts by weight with respect to 100 parts by weight of the cyclohexane polyester-based substance:

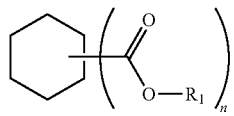

[Chemical Formula 1]

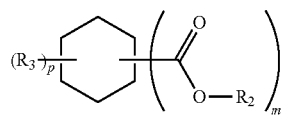

[Chemical Formula 2]

wherein in Chemical Formulas 1 and 2, $R_1$ and $R_2$ are each independently a C4 to C10 alkyl group, $R_3$ is a methyl group, n is 2 or 3, m is an integer from 0 to 2, p is an integer from 0 to 3, m+p is an integer from 0 to 3, and n−m is an integer from 1 to 3.

According to an embodiment of the present invention, the number (n) of ester groups in the cyclohexane polyester-based substance is 2 or 3. When there are two ester groups, the ester groups can be bonded to 1- and 3-positions or 1- and 4-positions of carbons of cyclohexane, and when there are three ester groups, the ester groups can be bonded to 1-, 2-, and 4-positions of carbons of cyclohexane.

Specifically, the cyclohexane polyester-based substance can be selected from among compounds of the following Chemical Formula 1-1 to Chemical Formula 1-3:

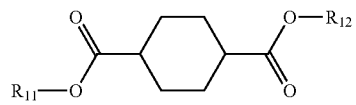

[Chemical Formula 1-1]

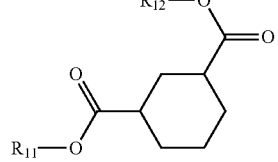

[Chemical Formula 1-2]

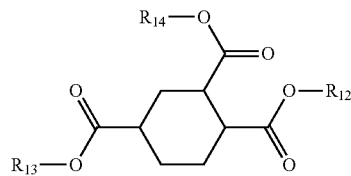

[Chemical Formula 1-3]

wherein in Chemical Formulas 1-1 to 1-3, $R_{11}$ to $R_{15}$ are each independently a C4 to C10 alkyl group.

$R_{11}$ to $R_{15}$ in Chemical Formula 1-1 to Chemical Formula 1-3 can be defined as the same as $R_1$ in Chemical Formula 1. As described above, $R_{11}$ to $R_{15}$ are a C4 to C10 alkyl group, and the alkyl group can be a linear alkyl group or a branched alkyl group in which branches are bonded to the main chain. The following definition and embodiment of $R_1$ can also be applied to $R_{11}$ to $R_{15}$.

The cyclohexane polyester-based substance in which $R_1$ is a C4 to C10 alkyl group exhibits a superior balance among physical properties compared to when the number of carbon atoms of an alkyl group is out of the above-described range. When an alkyl group bonded to each ester group has less than 4 carbon atoms, migration, volatile loss, tensile strength, and an elongation rate can be significantly degraded, and when an alkyl group has greater than 10 carbon atoms, there is an increased possibility that plasticization efficiency, an elongation rate, an absorption rate, and the like are degraded. Therefore, a cyclohexane polyester-based substance in which an alkyl group having 4 to 10 carbon atoms is bonded to an ester group is preferred.

$R_1$ can be, for example, a n-butyl group (abbreviated as B), an isobutyl group (abbreviated as IB), a n-pentyl group (abbreviated as P), an isopentyl group (abbreviated as IP), a n-hexyl group (abbreviated as Hx), an isohexyl group (abbreviated as IHx), a n-heptyl group (abbreviated as Hp), an isoheptyl group (abbreviated as IHp), a n-octyl group (abbreviated as nO), an isooctyl group (abbreviated as IO), a 2-ethylhexyl group (abbreviated as EH), a n-nonyl group (abbreviated as N), an isononyl group (abbreviated as IN), a n-decyl group (abbreviated as nD), an isodecyl group (abbreviated as ID), a 2-propylheptyl group (abbreviated as PH), or the like. Among linear or branched alkyl groups having 4 to 10 carbon atoms, the above-listed alkyl groups are preferred in consideration of the supply and demand of raw materials.

$R_1$ is preferably a C5 to C10 alkyl group, and can be, for example, a n-pentyl group, an isopentyl group, a n-hexyl group, an isohexyl group, an isoheptyl group, a 2-ethylhexyl group, a n-nonyl group, an isononyl group, or a 2-propylheptyl group. These substituents can be preferred not only to lower manufacturing costs in terms of the supply and demand of raw materials but also to balance physical properties beneficial for commercialization, such as migration, thermal stability, plasticization efficiency, and the like.

According to an embodiment of the present invention, the perhydride includes one or more compounds of the following Chemical Formula 2:

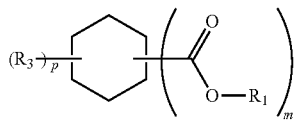

[Chemical Formula 2]

wherein in Chemical Formula 2, $R_2$ is a C4 to C10 alkyl group, $R_3$ is a methyl group, m is an integer from 0 to 2, p is an integer from 0 to 3, and m+p is an integer from 1 to 3.

The perhydride can include one or more types of compounds, preferably two or more types of compounds. When the perhydride is included in a plasticizer composition, plasticization efficiency can be improved, and migration upon compression and migration upon stress can also be expected to be improved. Furthermore, since there is no need to carry out separation and purification processes and the process is thus simplified, cost competitiveness of the finished product can be improved.

The perhydride includes the compound of Chemical Formula 2 which is derived from the above-described compound of Chemical Formula 1, so that it can have a relatively low molecular weight or less steric hindrance compared to the cyclohexane polyester-based substance.

When a specific amount of the perhydride is included along with the cyclohexane polyester-based substance in the plasticizer composition, it can be advantageous for maintaining the overall quality level even when a high-molecular-weight raw material to be hydrogenated is not completely hydrogenated, which provides an effect of expanding the quality range in the use of the cyclohexane polyester-based substance as a raw material of a plasticizer, and it also is possible to concomitantly simplify a hydrogenation process and omit a purification process of a reaction product, which provides an effect of considerably reducing manufacturing costs of an environmentally friendly plasticizer.

In the compound of Chemical Formula 2, $R_2$ can be defined as the same as $R_1$ in Chemical Formula 1 and can substantially be the same substituent as $R_1$.

In addition, in the relationship between the compound of Chemical Formula 1 and the compound of Chemical Formula 2, when n is 2, m can be 0 or 1, p can be an integer from 0 to 2, m+p can be an integer from 0 to 2, and n−m can be 1 or 2, and when n is 3, m can be an integer from 0 to 2, p can be an integer from 0 to 3, m+p can be an integer from 0 to 3, and n−m can be an integer from 1 to 3.

Additionally, the number of ester groups in the compound of Chemical Formula 2 can be one or two less than that in the compound of Chemical Formula 1. Specifically, when the compound of Chemical Formula 1 includes a diester, there can be no ester group or one ester group in the compound of Chemical Formula 2 (i.e., when n is 2, m is 0 or 1 (p is an integer from 0 to 2) and n−m is 1 or 2), and when the compound of Chemical Formula 1 includes a triester, there can be no ester group or one or two ester groups in the compound of Chemical Formula 2 (i.e., when n is 3, m is an integer from 0 to 2 (p is an integer from 0 to 3) and n−m is an integer from 1 to 3). In addition, the sum (m+p) of the number (m) of ester groups and the number (p) of alkyl groups, which are substituted in the compound of Chemical Formula 2, can be equal to, or one or two less than, the number (n) of ester groups in the compound of Chemical Formula 1.

Specifically, the compound of Chemical Formula 2 can be derived from by-products produced by hydrogenating cyclohexanepolycarboxylic acid which can be used as a raw material in the preparation of the compound of Chemical Formula 1. That is, the compound of Chemical Formula 2 can be a compound produced by substituting 1 to 3 carboxyl groups (1 or 2 carboxyl groups in the case of a diester and 1, 2 or 3 carboxyl groups in the case of a triester) with hydrogen (when p is 0) or a methyl group (when p is 1 to 3; p is 1 or 2 in the case of a diester and p is 1, 2, or 3 in the case of a triester) due to excessive reduction during reduction of 2 or 3 carboxyl groups and involving the excessively reduced substance as a reactant in esterification.

More specifically, the perhydride can include one or more compounds selected from among compounds of the following Chemical Formulas 2-1 to 2-11:

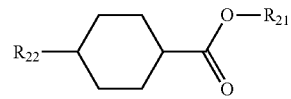

[Chemical Formula 2-1]

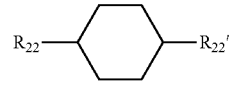

[Chemical Formula 2-2]

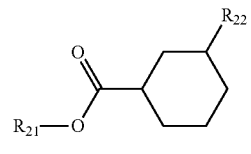

[Chemical Formula 2-3]

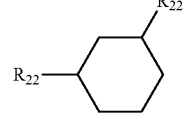

[Chemical Formula 2-4]

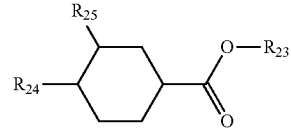

[Chemical Formula 2-5]

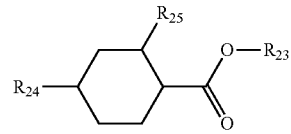

[Chemical Formula 2-6]

-continued

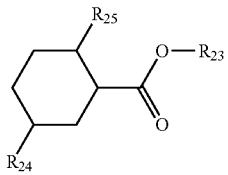

[Chemical Formula 2-7]

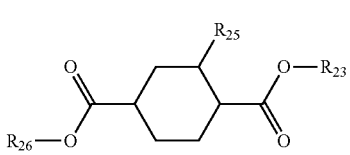

[Chemical Formula 2-8]

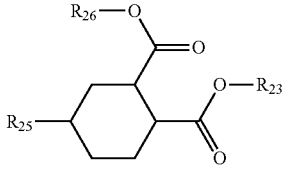

[Chemical Formula 2-9]

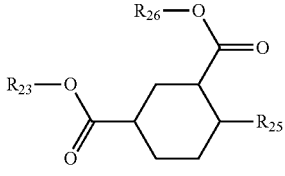

[Chemical Formula 2-10]

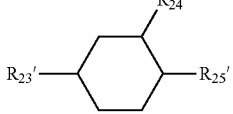

[Chemical Formula 2-11]

wherein in Chemical Formulas 2-1 to 2-11:

$R_{21}$, $R_{23}$, and $R_{26}$ are each independently a C4 to C10 alkyl group; and $R_{22}$, $R_{24}$, $R_{25}$, $R_{22}'$, $R_{23}'$, $R_{24}'$, and $R_{25}'$ are each independently hydrogen or a methyl group.

$R_{21}$, $R_{23}$, and $R_{26}$ in Chemical Formulas 2-1 to 2-8 can be the same as $R_2$ in Chemical Formula 2, and therefore, all descriptions about the definition and embodiment of $R_1$ in Chemical Formula 1 can also be applied to $R_{21}$, $R_{23}$, and $R_{26}$.

In addition, $R_{22}$, $R_{24}$, $R_{25}$, $R_{22}'$, $R_{23}'$, $R_{24}'$, and $R_{25}'$ can each independently be hydrogen or a methyl group and can be the same as $R_3$ in Chemical Formula 2.

When p is 1: $R_{22}$ in Chemical Formula 2-1 or Chemical Formula 2-3 can be a methyl group; only one of $R_{22}$ and $R_{22}'$ in Chemical Formula 2-2 or Chemical Formula 2-4 can be a methyl group; any one of $R_{24}$ and $R_{25}$ in Chemical Formulas 2-5 to 2-10 can be hydrogen and the other is a methyl group; and any one of $R_{23}'$, $R_{24}'$, and $R_{25}'$ in Chemical Formula 2-11 can be a methyl group.

When p is 2: $R_{24}$ and $R_{25}$ in Chemical Formula 2-5 to Chemical Formula 2-10 can be a methyl group; and two of $R_{23}'$, $R_{24}'$, and $R_{25}'$ in Chemical Formula 2-11 can be a methyl group. In addition, when p is 0: hydrogen is bonded at a $R_3$ position; and $R_{22}$, $R_{24}$, $R_{25}$, $R_{22}'$, $R_{23}'$, $R_{24}'$, and $R_{25}'$ in all of Chemical Formula 2-1 to Chemical Formula 2-11 can be hydrogen.

According to an embodiment of the present invention, the perhydride is included in an amount from 0.1 to 10 parts by weight with respect to 100 parts by weight of the cyclohexane polyester-based substance. When the content of the perhydride is within the above-described range, the effect of improving thermal stability, tensile strength, and an elongation rate is maximized and can be expected to be remarkably increased beyond an equivalent level.

Specifically, the perhydride is preferably included in an amount from 0.1 to 8.0 parts by weight, more preferably 0.1 to 6.0 parts by weight or 0.1 to 5.0 parts by weight, and even more preferably 0.5 to 4.0 parts by weight with respect to 100 parts by weight of the cyclohexane polyester-based substance.

For example, two or more types of the perhydrides can be included. As examples of the perhydride, the compound of Chemical Formula 2-1 can include cyclohexane monoalkyl ester and 4-methylcyclohexane monoalkyl ester; the compound of Chemical Formula 2-2 can be the same as described above, except that 3-methylcyclohexane monoalkyl ester is included instead of 4-methylcyclohexane monoalkyl ester; and furthermore, a compound selected from among compounds of Chemical Formula 2-5 to Chemical Formula 2-10 can be appropriately controlled such that a total amount thereof is within the above-described content range of the perhydride. For reference, the alkyl of the "monoalkyl ester" can correspond to the above-described substituent $R_2$ in Chemical Formula 2.

When one or more types, preferably, two or more types of the perhydrides are included and the content thereof is controlled to a specific content as described above, the above-described effects can be further maximized, and in this case, a plasticizer composition capable of realizing the most optimum physical properties can be obtained.

The plasticizer composition according to an embodiment of the present invention can be a mixture of the cyclohexane polyester-based substance and the perhydride, wherein, specifically, the cyclohexane polyester-based substance and the perhydride are closely related to each other and can be formed in a specific combination.

Specifically, in the plasticizer composition, the cyclohexane polyester-based substance can be the compound of Chemical Formula 1-1, and the perhydride can include one or more compounds of Chemical Formula 2-1 and also include the compound of Chemical Formula 2-2.

In this case, the cyclohexane polyester-based substance which is the compound of Chemical Formula 1-1 can be present as a mixture of isomers, and can be a mixture of isomers of the following structures:

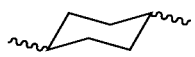

[Trans isomer]

[Cis isomer]

That is, when the cyclohexane polyester-based substance included in the plasticizer composition according to the present invention is the compound of Chemical Formula 1-1, it can be a mixture of the above-described isomers.

Alternatively, in the plasticizer composition, the cyclohexane polyester-based substance can be the compound of Chemical Formula 1-2, and the perhydride can include one or more compounds of Chemical Formula 2-2 and also include the compound of Chemical Formula 2-4.

Further alternatively, the cyclohexane polyester-based substance can be the compound of Chemical Formula 1-3, and the perhydride can include one or more compounds selected among compounds of Chemical Formulas 2-5 to 2-10 and also include the compound of Chemical Formula 2-11.

The above-described combinations can be obtained as a combination of mutually related substances which are products of a preparation method to be described below, but the possibility of a combination different from the above-described combinations is not excluded.

The plasticizer composition according to an embodiment of the present invention can further include an aromatic polyester-based substance which can be derived from substances that are not reacted in the hydrogenation of a raw material. In this case, the aromatic polyester-based substance preferably remains in an amount of 0.5 wt % or more with respect to the total weight of the plasticizer composition, and it can be preferred that the aromatic polyester-based substance does not exceed 15 wt % of the total weight of the plasticizer composition. When the content of the aromatic polyester-based substance is within the above-described range, plasticization efficiency, processability, melting ability, and the like are excellent, and the preparation process can be simplified due to mild hydrogenation conditions.

Method of Preparing Plasticizer Composition

According to another embodiment of the present invention, there is provided a method of preparing a plasticizer composition, the method including: hydrogenating any one aromatic polycarboxylic acid selected from the group consisting of isophthalic acid, terephthalic acid, and trimellitic acid to obtain a hydride including cyclohexanepolycarboxylic acid; and esterifying the hydride with a primary alkyl alcohol, wherein the primary alkyl alcohol has a C4 to C10 alkyl, and the cyclohexanepolycarboxylic acid is cyclohexane 1,3-dicarboxylic acid, cyclohexane 1,4-dicarboxylic acid, or cyclohexane 1,2,4-tricarboxylic acid. The method is a method of preparing the above-described plasticizer composition.

According to an embodiment of the present invention, the step of hydrogenating any one aromatic polycarboxylic acid selected from the group consisting of isophthalic acid, terephthalic acid, and trimellitic acid to obtain a hydride including cyclohexanepolycarboxylic acid can be performed first.

Specifically, a reactant used in the hydrogenation is an aromatic polycarboxylic acid such as isophthalic acid, terephthalic acid, or trimellitic acid, and also includes a derivative thereof, and any derivative can be applied as a raw material as long as it can be reduced by hydrogenation to produce cyclohexanepolycarboxylic acid.

The hydrogenation can be a reaction in which aromatic polycarboxylic acid is hydrogenated in the presence of a metallic catalyst to completely eliminate the aromaticity of a benzene ring and thus converted to cyclohexanepolycarboxylic acid. As an aromatic carboxylic acid to be used in the hydrogenation, any aromatic carboxylic acid can be applied without any particular problem as long as it is commercially available in the related art.

The hydrogenation is a reaction in which hydrogen is added in the presence of a metallic catalyst to eliminate all the double bonds of a benzene ring of the aromatic carboxylic acid. The hydrogenation can be a kind of reduction reaction and can be performed in the presence of a metallic catalyst. The hydrogenation conditions can include all the conventional hydrogenation conditions capable of hydrogenating only a benzene ring without affecting carboxylic acid bonded in benzene.

The hydrogenation can be performed by further including an organic solvent such as ethanol or the like, but the present invention is not limited thereto. The metallic catalyst can be a catalyst commonly used to hydrogenate a benzene ring, that is, a catalyst in which a noble metal such as Ru, Pt, Pd, or the like is supported in carbon, alumina, or the like, but the present invention is not limited thereto as long as it catalyzes a hydrogenation reaction as described above.

Since the hydrogenation that is performed in the presence of hydrogen and a metallic catalyst is generally performed at high pressure, it is difficult to control the reaction. For this reason, various types of by-products can be produced, and the above-described perhydride can be derived from these by-products.

In the present invention, it is necessary to pay attention to, among various by-products, substances produced by excessively reducing a carboxyl group of the aromatic polycarboxylic acid.

Generally in the hydrogenation of aromatic polycarboxylic acid, it is most preferable that only the unsaturated bond of an aromatic ring except polycarboxylic acid is hydrogenated, but by-products produced by a side reaction such as excessive reduction (excessive hydrogenation) or unreacted substances generally result from the hydrogenation. The by-products except a desired product are usually completely eliminated or are suppressed to a maximum extent by adjusting the reaction conditions.

That is, the by-products are generally eliminated because they affect the purity of cyclohexanepolycarboxylic acid which is a desired product, but it has been found in the present invention that the perhydride has an effect on performance of a plasticizer. Accordingly, the by-products are not eliminated but are allowed to participate in the reaction so that performance of a product prepared using the hydride as a plasticizer can be enhanced, and simultaneously, it can be advantageous in terms of costs or facilities for a purification process since there is no need to eliminate by-products. Furthermore, cost competitiveness of a finished product can also be ensured.

A perhydride produced from the aromatic polycarboxylic acid can be one or more selected from among cyclohexane, methylcyclohexane, 1,3-dimethylcyclohexane, cyclohexane monocarboxylic acid, and 3-methylcyclohexane monocarboxylic acid when isophthalic acid is used, one or more selected from among cyclohexane, methylcyclohexane, 1,4-dimethylcyclohexane, cyclohexane monocarboxylic acid, and 4-methylcyclohexane monocarboxylic acid when terephthalic acid is used, or any substance that can be produced by reacting one to three of three carboxyl groups in a reduction reaction when trimellitic acid is used. In this case, the one to three carboxyl groups to be reduced can be converted to hydrogen or a methyl group.

Since such a perhydride included among the products is converted to the above-described perhydride including the compound of Chemical Formula 2, considering that it is preferred that the perhydride is included in an amount from 0.1 to 10 parts by weight with respect to 100 parts by weight of the cyclohexane polyester-based substance, the content of the perhydride can be controlled by adjusting the hydrogenation conditions, so that the content of the perhydride included in a final product can also be appropriately controlled.

That is, by including the perhydride produced from the aromatic polycarboxylic acid along with the cyclohexanepolycarboxylic acid, the effects of the present invention can be realized through the mechanism as mentioned in the description of the plasticizer composition. In addition, this has a considerable technical significance in that by-products are applied as an additive capable of improving the performance of a hydrogenated plasticizer, which departs from the common technical knowledge in the art.

According to an embodiment of the present invention, in addition to the hydride produced in the hydrogenation, an aromatic polycarboxylic acid as a unreacted substance that has not been subjected to the hydrogenation can also be present. A weight ratio of the unreacted aromatic polycarboxylic acid that has not been subjected to the hydrogenation and the hydride can be 99:1 to 1:99, and within this range, the unreacted aromatic polycarboxylic acid can be further included in addition to the hydride. The weight ratio can be controlled according to a hydrogenation conversion rate. However, in the present invention, the above-described effects can be realized according to components included in the hydrogenated substance and contents thereof, and therefore, how much aromatic polycarboxylic acid is substantially included can be irrelevant.

According to an embodiment of the present invention, the step of esterifying the hydride and a primary alkyl alcohol can be performed after the hydrogenation.

Specifically, the hydride including cyclohexanepolycarboxylic acid and a perhydride thereof is subjected to direct esterification with a primary alkyl alcohol. In this case, a carboxyl group of the cyclohexanepolycarboxylic acid and one or two carboxyl groups of the perhydride are esterified with the primary alkyl alcohol.

Among the perhydrides, cyclohexane, methylcyclohexane, or dimethylcyclohexane, which is produced by hydrogenating all the ester groups in aromatic polycarboxylic acid, can also be included, but is not involved in the esterification even though it is included in raw materials of the reaction. Although this perhydride is not substantially involved in the reaction, it can serve, due to its low boiling point, as a substance in an entrained form capable of eliminating water generated during the esterification from the system at relatively low temperature in a short time, which can provide effects such as an improvement in reactivity in esterification with an alcohol, an improvement in manufacturing cost by saving energy, and the like.

An alkyl group, which is bonded while the carboxyl groups are esterified, is derived from the primary alkyl alcohol, and an "alkyl" of the primary alkyl alcohol can be the same as $R_1$ and $R_2$ defined in Chemical Formulas 1 and 2. Therefore, descriptions about the embodiment and features thereof are not repeated below.

The esterification can be performed by adding the hydride to a primary alkyl alcohol and then reacting the resultant mixture in the presence of a catalyst under a nitrogen atmosphere; removing an unreacted alcohol and neutralizing an unreacted carboxylic acid; and performing dehydration through vacuum distillation and filtration.

The primary alkyl alcohol can be used in an amount from 150 to 500 mol %, 200 to 400 mol %, 200 to 350 mol %, 250 to 400 mol %, or 270 to 330 mol % with respect to 100 mol % of the hydride.

The catalyst can be, for example, one or more selected from among acidic catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid, an alkyl sulfate, and the like; metal salts such as aluminum lactate, lithium fluoride, potassium chloride, cesium chloride, calcium chloride, iron chloride, aluminum phosphate, and the like; metal oxides such as a heteropoly acid and the like; natural/synthetic zeolites; cation and anion exchange resins; and organic metals such as a tetra alkyl titanate and polymers thereof and the like. As a specific example, the catalyst can be a tetra alkyl titanate.

The usage amount of the catalyst can be varied according to its type. For example, in the case of a homogeneous catalyst, the catalyst can be used in an amount from 0.01 to 5 wt %, 0.01 to 3 wt %, 1 to 5 wt %, or 2 to 4 wt % with respect to 100 wt % of the total reactants, and in the case of a heterogeneous catalyst, the catalyst can be used in an amount from 5 to 200 wt %, 5 to 100 wt %, 20 to 200 wt %, or 20 to 150 wt % with respect to a total amount of the reactants.

The esterification is performed at 80° C. to 270° C., preferably 150° C. to 250° C. for 10 minutes to 10 hours, preferably 30 minutes to 8 hours, and more preferably 1 to 6 hours. Within the above-described ranges of temperature and time, a plasticizer composition can be effectively obtained.

In addition, according to an embodiment of the present invention, the plasticizer composition can further include an aromatic polyalkyl ester-based substance in an amount from 0.5 part by weight or less with respect to 100 parts by weight of the plasticizer composition.

The inclusion of the aromatic polyalkyl ester-based substance in an amount of 0.5 part by weight or less can mean that it is substantially present as a by-product in the final plasticizer composition and is not an additionally included aromatic polyalkyl ester-based substance. However, it is also not intended to exclude a plasticizer composition prepared by further including an aromatic polyalkyl ester-based substance.

The aromatic polyalkyl ester-based substance can be derived from unreacted substances during the hydrogenation of aromatic carboxylic acid, and can be, for example, dialkyl isophthalate derived from isophthalic acid, dialkyl terephthalate derived from terephthalic acid, or trialkyl trimellitate derived from trimellitic acid.

In this case, the alkyl can be an alkyl group derived from the primary alkyl alcohol, which is the same alkyl group as $R_1$ and $R_2$ of Chemical Formulas 1 and 2, and therefore, descriptions about the specific types and features of the alkyl group are omitted below.

Resin Composition

According to still another embodiment of the present invention, there is provided a resin composition including the above-described plasticizer composition and a resin.

The resin can be any resin known in the art. For example, a mixture of one or more selected from the group consisting of a straight vinyl chloride polymer, a paste vinyl chloride polymer, an ethylene-vinyl acetate copolymer, an ethylene polymer, a propylene polymer, polyketone, polystyrene, polyurethane, natural rubber, synthetic rubber, and a thermoplastic elastomer can be used, but the present invention is not limited thereto.

The plasticizer composition can be included in an amount from 5 to 150 parts by weight, preferably, 5 to 130 parts by weight or 10 to 120 parts by weight with respect to 100 parts by weight of the resin.

In general, a resin composition in which a plasticizer composition is used can be subjected to melt processing or plastisol processing to prepare a resin product, and the resin for melt processing and the resin for plastisol processing can be produced differently according to a polymerization method.

For example, when used in melt processing, a vinyl chloride polymer is prepared through suspension polymerization or the like and thus used as a solid-phase resin particle having a large average particle diameter. In this case, the vinyl chloride polymer is called a straight vinyl chloride polymer. When used in plastisol processing, a vinyl chloride polymer is prepared through emulsion polymerization or the like and thus used as a fine sol-phase resin particle. In this case, the vinyl chloride polymer is called a paste vinyl chloride polymer.

In the case of the straight vinyl chloride polymer, the plasticizer is preferably included in an amount from 5 to 80 parts by weight with respect to 100 parts by weight of the polymer, and in the case of the paste vinyl chloride polymer, the plasticizer is preferably included in an amount from 40 to 120 parts by weight with respect to 100 parts by weight of the polymer.

The resin composition can further include a filler. The filler can be included in an amount from 0 to 300 parts by weight, preferably 50 to 200 parts by weight, and more preferably 100 to 200 parts by weight with respect to 100 parts by weight of the resin.

The filler can be any filler known in the art without particular limitation. For example, a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate, and barium sulfate can be used.

In addition, the resin composition can further include other additives such as a stabilizer and the like as necessary. The additives such as a stabilizer and the like can be included, for example, in an amount from 0 to 20 parts by weight, preferably 1 to 15 parts by weight with respect to 100 parts by weight of the resin.

The stabilizer can be, for example, a calcium-zinc (Ca—Zn)-based stabilizer such as a complex stearate of calcium and zinc and the like or a barium-zinc (Ba—Zn)-based stabilizer, but the present invention is not particularly limited thereto.

The resin composition can be applied to both melt processing and plastisol processing as described above, wherein the melt processing can be, for example, calendering processing, extrusion processing, or injection processing, and the plastisol processing can be coating processing or the like.

EXAMPLES

Hereinafter, the present invention will be described in detail with reference to embodiments so that those skilled in the art can easily carry out the present invention. However, the present invention can be embodied in several different forms, and therefore, is not limited to embodiments described herein.

1-1. Cyclohexane 1,4-diester-based Substance

Example 1-1

A predetermined volume of a silica-supported palladium catalyst was held in a 1.5 L pressure vessel equipped with a stirrer, and 25 g of terephthalic acid as a reactant and 1 L of water were injected and stirred while injecting hydrogen by means of a mass flow meter. While the temperature inside the reaction vessel was raised up to 200° C. and an internal hydrogen pressure was maintained at 80 bar, the mixture was allowed to react for one hour. After completion of the reaction, a reaction product in the reaction vessel was recovered using methanol and purified. Afterward, esterification was performed in the presence of a Ti-based catalyst using 2-ethylhexanol in an amount of 300 mol % with respect to the hydrogenation product, followed by purification to obtain an ester product in the form of a composition.

Example 1-2

A predetermined volume of a silica-supported palladium catalyst was held in a 1.5 L pressure vessel equipped with a stirrer, and 25 g of terephthalic acid as a reactant and 1 L of water were injected and stirred while injecting hydrogen by means of a mass flow meter. While the temperature inside the reaction vessel was raised up to 230° C. and an internal hydrogen pressure was maintained at 80 bar, the mixture was allowed to react for one hour. After completion of the reaction, a reaction product in the reaction vessel was recovered using methanol and purified. Afterward, esterification was performed in the presence of a Ti-based catalyst using 2-ethylhexanol in an amount of 300 mol % with respect to the hydrogenation product, followed by purification to obtain an ester product in the form of a composition.

Examples 1-3 and 1-4

A predetermined volume of a silica-supported palladium catalyst was held in a 1.5 L pressure vessel equipped with a stirrer, and 25 g of terephthalic acid as a reactant and 1 L of water were injected and stirred while injecting hydrogen by means of a mass flow meter. While the temperature inside the reaction vessel was raised up to 230° C. and an internal hydrogen pressure was maintained at 80 bar, the mixture was allowed to react for two hours. After completion of the reaction, a reaction product in the reaction vessel was recovered using methanol and subjected to vacuum distillation such that the content of a perhydride was adjusted as shown in Table 1 below. Afterward, esterification was performed in the presence of a Ti-based catalyst using 2-ethylhexanol in an amount of 300 mol % with respect to the hydrogenation product, followed by purification to obtain an ester product in the form of a composition.

Comparative Example 1-1

A conventional plasticizer, GL300 (di(2-ethylhexyl) terephthalate) commercially available from LG Chem Ltd., was used.

Comparative Examples 1-2 and 1-3

A predetermined volume of a silica-supported palladium catalyst was held in a 1.5 L pressure vessel equipped with a stirrer, and 25 g of terephthalic acid as a reactant and 1 L of water were injected and stirred while injecting hydrogen by means of a mass flow meter. While the temperature inside the reaction vessel was raised up to 230° C. and 260° C. in Comparative Examples 1-2 and 1-3, respectively, and an internal hydrogen pressure was maintained at 80 bar, the mixture was allowed to react for two hours. After completion of the reaction, a reaction product in the reaction vessel was recovered using methanol and subjected to vacuum distillation such that the content of a perhydride was adjusted as shown in Table 1 below. Afterward, esterification was performed in the presence of a Ti-based catalyst using 2-ethylhexanol in an amount of 300 mol % with respect to the hydrogenation product, followed by purification to obtain an ester product in the form of a composition.

Comparative Example 1-4

510 g of 1,4-cyclohexanedicarboxylic acid (TCI Chemicals), 1,170 g of 2-ethylhexanol, and 1.5 g of tetraisopropyl titanate (TiPT) as a catalyst were put into a 3 L flask equipped with a stirrer, a condenser, and a decanter, and esterification was initiated while gradually raising the temperature of the flask and terminated when an acid value of the final reaction product reached 0.1. Afterward, distillation, neutralization/washing, dehydration, and filtration processes were performed to obtain 1,160 g of 1,4-diethylhexyl cyclohexanoate.

The compositions of plasticizer compositions according to Examples and Comparative Examples are shown in Table 1 below.

TABLE 1

|  | Desired product[1] | Perhydride[2] |
| --- | --- | --- |
| Example 1-1 | 86.1 | 1.631 |
| Example 1-2 | 85.8 | 3.741 |
| Example 1-3 | 87.2 | 0.583 |
| Example 1-4 | 82.3 | 9.588 |
| Comparative Example 1-1 | — | — |
| Comparative Example 1-2 | 78.6 | 12.646 |
| Comparative Example 1-3 | 89.5 | 11.596 |
| Comparative Example 1-4 | 99.7 | 0.027 |

[1]Di(2-ethylhexyl) cyclohexane 1,4-diester (wt %)
[2]Mixed content of cyclohexyl (2-ethyl)hexanoate and 4-methylcyclohexyl-1-(2-ethyl) hexanoate (parts by weight based on 100 parts by weight of di(2-ethylhexyl) cyclohexane 1,4-diester)

1-2. Evaluation of Plasticizer Composition

For specimen preparation, in accordance with ASTM D638, 100 parts by weight of polyvinyl chloride (LS100 manufactured by LG Chem Ltd.), 40 parts by weight of each of the plasticizer compositions prepared in Examples and Comparative Examples, and 3 parts by weight of a stabilizer (BZ153T manufactured by SONGWON) were mixed while stirring at 98° C. and 700 rpm, and the resultant mixture was subjected to roll-milling at 160° C. for 4 minutes and pressed using a press at 180° C. for 3 minutes (low pressure) and for 2.5 minutes (high pressure), thereby preparing 1 mm-thick and 3 mm-thick specimens.

<Test Items>

Measurement of Hardness (Shore "A" and Shore "D")

In accordance with ASTM D2240, the hardness of a 3 mm-thick specimen was measured for 10 seconds.

Measurement of Migration Loss (%)

In accordance with KSM-3156, glass plates were attached to both sides of a 1 mm-thick specimen, and a load of 1 kgf/cm² was then applied thereto. The specimen was placed in a hot-air convection oven (80° C.) for 72 hours, then taken out of the oven, and cooled at room temperature. Afterward, the glass plates attached to both sides of the specimen were removed, weights of the specimen before being placed in and after taken out of the oven were measured, and the resultant weights were substituted into the following Equation 1 to calculate a migration loss value.

Migration loss (%)=[(Initial weight of specimen before being placed in oven)−(Weight of specimen after taken out of oven)]/(Initial weight of specimen before being placed in oven) ×100  <Equation 1>

Measurement of Volatile Loss (%)

A 1 mm-thick specimen was exposed to 80° C. for 72 hours and weighed. Afterward, the resultant weight was substituted into the following Equation 2 to calculate a volatile loss value.

Volatile loss (%)=[(Initial weight of specimen)−(Weight of specimen after being exposed)]/(Initial weight of specimen) ×100  <Equation 2>

Measurement of Tensile Strength (kg/cm²)

In accordance with ASTM D638, a 1 mm-thick specimen was pulled at a cross head speed of 200 mm/min using a universal testing machine (UTM; 4466 manufactured by Instron), and a time point at which the specimen was broken was then determined.

Measurement of Elongation Rate (%)

In accordance with ASTM D638, a 1 mm-thick specimen was pulled at a cross head speed of 200 mm/min using a universal testing machine (UTM; 4466 manufactured by Instron), and a time point at which the specimen was broken was then determined. Afterward, a length at the time point was substituted into the following Equation 3 to calculate an elongation rate.

Elongation rate (%)=[(Length at the time point when specimen was broken)/(Initial length)]×100  <Equation 3>

Measurement of UV Resistance

In accordance with ASTM D4329, a specimen was mounted at a specimen holder in a QUV accelerated weathering tester (QUV/se manufactured by Q-LAB) and exposed to UV radiation (UVA-340 lamp) at a predetermined temperature (60° C.) for a predetermined time. After 400 hours of the test, the specimen was taken out, and the color change before and after the test was measured. A lower value indicates that there was almost no discoloration, and thus it was evaluated that as a value is low, UV resistance was excellent.

TABLE 2

| Classification | Hardness | | Migration loss (%) | Volatile loss (%) | Tensile strength (kg/cm²) | Elongation rate (%) | UV resistance (ΔE) |
| --- | --- | --- | --- | --- | --- | --- | --- |
|  | Shore 'A' | Shore 'D' |  |  |  |  |  |
| Example 1-1 | 90.9 | 45.3 | 3.37 | 0.73 | 243.5 | 342.1 | 1.4 |
| Example 1-2 | 90.7 | 45.2 | 3.40 | 0.92 | 241.7 | 337.0 | 1.4 |
| Example 1-3 | 90.7 | 45.3 | 3.02 | 0.58 | 245.1 | 349.1 | 1.3 |
| Example 1-4 | 90.8 | 45.4 | 3.56 | 1.84 | 244.0 | 338.1 | 1.6 |
| Comparative Example 1-1 | 94.2 | 50.3 | 4.78 | 0.70 | 238.6 | 320.4 | 7.6 |
| Comparative Example 1-2 | 90.8 | 45.4 | 4.69 | 3.22 | 228.0 | 319.5 | 2.0 |
| Comparative Example 1-3 | 90.7 | 45.5 | 4.32 | 3.08 | 237.9 | 326.9 | 2.1 |
| Comparative Example 1-4 | 90.8 | 45.2 | 3.52 | 0.98 | 242.5 | 324.5 | 1.3 |

Referring to Table 2, it can be seen that Comparative Example 1-1, which is a conventional environmentally-friendly di(2-ethylhexyl) terephthalate plasticizer, exhibited notably degraded properties in terms of plasticization efficiency and UV resistance, and also exhibited degraded properties in terms of migration, tensile strength, and an elongation rate compared to Examples.

In addition, it can be seen that Comparative Examples 1-2 and 1-3, in which the content of a perhydride exceeded 10 parts by weight with respect to 100 parts by weight of the desired product, exhibited degraded properties in terms of tensile strength and an elongation rate, and also exhibited significantly degraded properties in terms of migration loss and volatile loss. Additionally, it can be seen that Comparative Example 1-4, which is a conventional hydrogenation product including a very small amount of a perhydride, exhibited a degraded elongation rate and similar levels of other properties. However, when production costs of Comparative Example 1-4 and Examples were compared based on the amount of product used to obtain the same effect, at least 1.3 times the amount of plasticizers of Examples is required for the plasticizer of Comparative Example 1-4 to produce the same effect, which indicates that considering the production cost, there is a significant difference between the effects of Comparative Example 1-4 and Examples, and the difference is not just a matter of the difference in an elongation rate.

From these results, it can be seen that when a perhydride produced during the conversion process to a hydrogenated product is intentionally included in order to obtain improved plasticization efficiency and improved UV resistance compared to a conventional product, various properties as well as plasticization efficiency and UV resistance are improved, and furthermore, a purification process can be simplified to ensure cost competitiveness compared to a conventionally hydrogenated product.

2-1. Cyclohexane 1,3-diester-based Substance

Example 2-1

A cyclohexane 1,3-diester-based substance was prepared in the same manner as in Example 1-1 except that isophthalic acid (1,3-dicarboxylic acid) was used instead of terephthalic acid.

Example 2-2

A cyclohexane 1,3-diester-based substance was prepared in the same manner as in Example 1-2 except that isophthalic acid (1,3-dicarboxylic acid) was used instead of terephthalic acid.

Example 2-3

A cyclohexane 1,3-diester-based substance was prepared in the same manner as in Example 1-4 except that isophthalic acid (1,3-dicarboxylic acid) was used instead of terephthalic acid.

Comparative Example 2-1

A conventional plasticizer, GL300 (di(2-ethylhexyl) terephthalate) commercially available from LG Chem Ltd., was used.

Comparative Example 2-2

A cyclohexane 1,3-diester-based substance was prepared in the same manner as in Comparative Example 1-3 except that isophthalic acid (1,3-dicarboxylic acid) was used instead of terephthalic acid.

Comparative Example 2-3

A cyclohexane 1,3-diester-based substance was prepared in the same manner as in Comparative Example 1-4 except that 1,3-cyclohexane dicarboxylic acid was used instead of 1,4-cyclohexane dicarboxylic acid.

The compositions of plasticizer compositions according to Examples and Comparative Examples are shown in Table 3 below.

TABLE 3

|  | Desired product[1] | Perhydride[2] |
|---|---|---|
| Example 2-1 | 87.3 | 1.45 |
| Example 2-2 | 82.8 | 5.56 |
| Example 2-3 | 79.2 | 9.23 |
| Comparative Example 2-1 | — | — |
| Comparative Example 2-2 | 77.5 | 13.50 |
| Comparative Example 2-3 | 99.8 | 0.01 |

[1]Di(2-ethylhexyl) cyclohexane 1,3-diester (wt %)
[2]Cyclohexyl (2-ethyl)hexanoate and 3-methylcyclohexyl-1-(2-ethyl)hexanoate (parts by weight based on 100 parts by weight of di(2-ethylhexyl) cyclohexane 1,3-diester)

2-2. Evaluation of Plasticizer Composition

For specimen preparation, in accordance with ASTM D638, 100 parts by weight of polyvinyl chloride (LS100 manufactured by LG Chem Ltd.), 40 parts by weight of each of the plasticizer compositions prepared in Examples and Comparative Examples, and 3 parts by weight of a stabilizer (BZ153T manufactured by SONGWON) were mixed while stirring at 98° C. and 700 rpm, and the resultant mixture was subjected to roll-milling at 160° C. for 4 minutes and pressed using a press at 180° C. for 3 minutes (low pressure) and for 2.5 minutes (high pressure), thereby preparing 1 mm-thick and 3 mm-thick specimens.

In addition, the evaluation was performed in the same manner as in Section 1-2, and a stress test was performed as follows.

Stress Test (Stress Resistance)

A 2 mm-thick specimen in a bent state was left to stand at 23° C. for 72 hours, and a degree of migration (leaking degree) was then observed and expressed as a numerical value from 0 to 3. In this case, values closer to 0 indicate excellent characteristics.

TABLE 4

| Classification | Hardness Shore 'A' | Hardness Shore 'D' | Migration loss (%) | Volatile loss (%) | Tensile strength (kg/cm$^2$) | Elongation rate (%) | Stress test |
|---|---|---|---|---|---|---|---|
| Example 2-1 | 91.2 | 45.6 | 3.28 | 1.32 | 221.6 | 281.3 | 0.5 |
| Example 2-2 | 91.3 | 45.7 | 3.26 | 1.52 | 224.4 | 282.8 | 0.5 |
| Example 2-3 | 91.0 | 45.2 | 3.24 | 2.01 | 223.0 | 286.5 | 0.5 |
| Comparative Example 2-1 | 94.4 | 50.4 | 4.25 | 1.02 | 220.6 | 278.4 | 3.0 |
| Comparative Example 2-2 | 91.0 | 45.1 | 3.42 | 3.21 | 204.6 | 283.0 | 1.0 |
| Comparative Example 2-3 | 92.0 | 45.9 | 4.20 | 1.34 | 218.7 | 268.4 | 3.0 |

Referring to Table 4, it can be seen that when compared with Comparative Example 2-1 which is a conventional environmentally-friendly plasticizer, Examples exhibited a significant improvement in plasticization efficiency and stress resistance. In addition, it can be seen that Comparative Example 2-2, in which the content of a perhydride exceeded 10 parts by weight, exhibited significantly degraded properties in terms of volatile loss and tensile strength, and Comparative Example 2-3, in which the content of a perhydride was less than 0.1 part by weight which is a commonly included amount, exhibited degraded properties in terms of an elongation rate, stress resistance, and migration loss.

From these results, it can be seen that when a perhydride produced during the conversion process to a hydrogenated product is intentionally included in order to obtain improved plasticization efficiency and improved stress resistance compared to a conventional product, various properties as well as plasticization efficiency and stress resistance are improved, and furthermore, a purification process can be simplified to ensure cost competitiveness compared to a conventionally hydrogenated product.

3-1. Cyclohexane 1,2,4-triester-based Substance

Example 3-1

A cyclohexane 1,2,4-triester-based substance was prepared in the same manner as in Example 1-1 except that trimellitic acid (1,2,4-benzenetricarboxylic acid) was used instead of terephthalic acid.

Example 3-2

A cyclohexane 1,2,4-triester-based substance was prepared in the same manner as in Example 1-2 except that trimellitic acid (1,2,4-benzenetricarboxylic acid) was used instead of terephthalic acid.

Example 3-3

A cyclohexane 1,2,4-triester-based substance was prepared in the same manner as in Example 1-4 except that trimellitic acid (1,2,4-benzenetricarboxylic acid) was used instead of terephthalic acid.

Comparative Example 3-1

A conventional plasticizer, LGflex TOTM (tri(2-ethylhexyl) trimellitate) commercially available from LG Chem Ltd., was used.

Comparative Example 3-2

A cyclohexane 1,2,4-triester-based substance was prepared in the same manner as in Comparative Example 1-3 except that trimellitic acid (1,2,4-benzenetricarboxylic acid) was used instead of terephthalic acid.

Comparative Example 3-3

A cyclohexane 1,2,4-triester-based substance was prepared in the same manner as in Comparative Example 1-4 except that 1,2,4-cyclohexane tricarboxylic acid was used instead of 1,4-cyclohexane dicarboxylic acid.

The compositions of plasticizer compositions according to Examples and Comparative Examples are shown in Table 5 below.

TABLE 5

|  | Desired product[1] | Perhydride[2] |
|---|---|---|
| Example 3-1 | 86.0 | 2.23 |
| Example 3-2 | 81.2 | 7.52 |
| Example 3-3 | 80.5 | 9.10 |
| Comparative Example 3-1 | — | — |
| Comparative Example 3-2 | 78.4 | 12.02 |
| Comparative Example 3-3 | 99.6 | 0.03 |

[1] Tri(2-ethylhexyl) cyclohexane 1,2,4-triester (wt %)

[2] Parts by weight based on 100 parts by weight of tri(2-ethylhexyl) cyclohexane 1,2,4-triester 3-2. Evaluation of Plasticizer Composition For specimen preparation, in accordance with ASTM D638, 100 parts by weight of polyvinyl chloride (LS100 manufactured by LG Chem Ltd.), 40 parts by weight of each of the plasticizer compositions prepared in Examples and Comparative Examples, and 3 parts by weight of a stabilizer (BZ153T manufactured by SONGWON) were mixed while stirring at 98° C. and 700 rpm, and the resultant mixture was subjected to roll-milling at 160° C. for 4 minutes and pressed using a press at 180° C. for 3 minutes (low pressure) and for 2.5 minutes (high pressure), thereby preparing 1 mm-thick and 3 mm-thick specimens.

In addition, the evaluation was performed in the same manner as in Section 1-2.

Stress Test (Stress Resistance)

A 2 mm-thick specimen in a bent state was left to stand at 23° C. for 72 hours, and a degree of migration (leaking degree) was then observed and expressed as a numerical value of 0 to 3. In this case, values closer to 0 indicate excellent characteristics.

TABLE 6

| Classification | Hardness Shore 'A' | Hardness Shore 'D' | Migration loss (%) | Volatile loss (%) | Tensile strength (kg/cm$^2$) | Elongation rate (%) | Stress test | UV resistance (ΔE) |
|---|---|---|---|---|---|---|---|---|
| Example 3-1 | 96.1 | 53.9 | 1.69 | 0.47 | 223.7 | 294.6 | 0 | 1.6 |
| Example 3-2 | 96.0 | 53.4 | 1.60 | 0.60 | 224.5 | 295.6 | 0 | 1.8 |
| Example 3-3 | 95.9 | 53.4 | 1.55 | 0.65 | 223.0 | 301.2 | 0 | 1.8 |
| Comparative Example 3-1 | 98.7 | 55.4 | 2.13 | 0.42 | 222.7 | 294.5 | 1 | 6.5 |
| Comparative Example 3-2 | 95.9 | 53.3 | 1.98 | 1.12 | 217.3 | 281.4 | 0 | 2.2 |
| Comparative Example 3-3 | 96.8 | 54.5 | 1.56 | 0.45 | 223.1 | 280.6 | 0.5 | 1.6 |

Referring to Table 6, it can be seen that when compared with Comparative Example 3-1 which is a conventional plasticizer, Examples exhibited a significant improvement in plasticization efficiency and UV resistance. In addition, it can be seen that Comparative Example 3-2, in which the content of a perhydride exceeded 10 parts by weight, was poor in all properties, particularly, volatile loss and an elongation rate, and Comparative Example 3-3, in which the content of a perhydride was less than 0.1 part by weight which is a commonly included amount, exhibited degraded properties in terms of an elongation rate, stress resistance, and plasticization efficiency.

From these results, it can be seen that when a perhydride produced during the conversion process to a hydrogenated product is intentionally included in order to obtain improved plasticization efficiency and improved UV resistance compared to a conventional product, various properties as well as plasticization efficiency and stress resistance can be expected to be improved, and furthermore, a purification process can be simplified to ensure cost competitiveness compared to a conventionally hydrogenated product.

The invention claimed is:

1. A plasticizer composition comprising:
   a cyclohexane polyester-based substance which is a compound of one of the following Chemical Formula 1-1 to Chemical Formula 1-3; and
   a perhydride comprising a compound of the following Chemical Formula 2,
   wherein the perhydride is present in an amount from 0.1 to 10 parts by weight with respect to 100 parts by weight of the cyclohexane polyester-based substance:

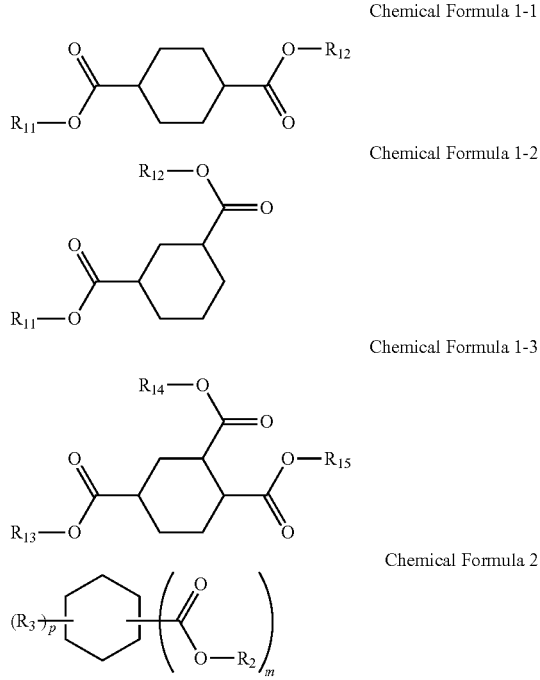

wherein:
$R_{11}$ to $R_{15}$ and $R_2$ are each independently a C4 to C10 alkyl group derived from a primary alcohol;
$R_3$ is a methyl group;
m is an integer of 1 or 2;
p is an integer of 1 or 2; and
m+p is an integer of 2 or 3.

2. The plasticizer composition of claim 1, wherein:
$R_{11}$ to $R_{15}$ and $R_2$ are each independently a C5 to C10 alkyl group; and
$R_3$ is a methyl group.

3. The plasticizer composition of claim 1, wherein the cyclohexane polyester-based substance is a compound of the following Chemical Formula 1-1, and the perhydride comprises one or more compounds of the following Chemical Formula 2-1:

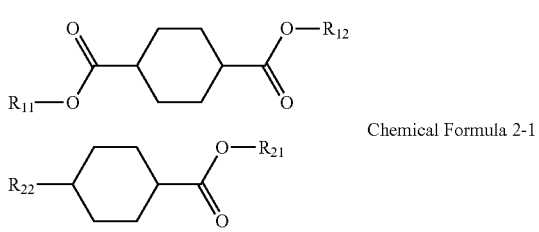

wherein $R_{11}$, $R_{12}$, and $R_{21}$ are each independently a C4 to C10 alkyl group, and $R_{22}$ is a methyl group.

4. The plasticizer composition of claim 3, wherein $R_{11}$, $R_{12}$ and $R_{21}$ are each independently selected from the group consisting of a n-butyl group, an isobutyl group, a n-pentyl group, an isopentyl group, a n-hexyl group, an isohexyl group, a n-heptyl group, an isoheptyl group, a n-octyl group, an isooctyl group, a 2-ethylhexyl group, a n-nonyl group, an isononyl group, a n-decyl group, an isodecyl group, and a 2-propylheptyl group.

5. The plasticizer composition of claim 3, wherein $R_{11}$, $R_{12}$ and $R_{21}$ are a 2-ethylhexyl group.

6. The plasticizer composition of claim 1, wherein:
the cyclohexane polyester-based substance is a compound of the following Chemical Formula 1-2; and
the perhydride comprises one or more compounds of the following Chemical Formula 2-2:

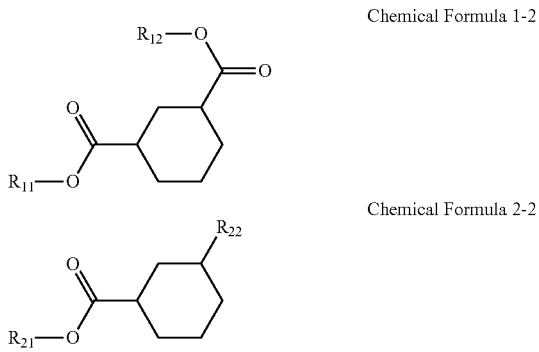

wherein $R_{11}$, $R_{12}$ and $R_{21}$ are each independently a C4 to C10 alkyl group, and $R_{22}$ is a methyl group.

7. The plasticizer composition of claim 6, wherein $R_{11}$ and $R_{12}$ are each independently selected from the group consisting of a n-butyl group, an isobutyl group, a n-pentyl group, an isopentyl group, a n-hexyl group, an isohexyl group, a n-heptyl group, an isoheptyl group, a n-octyl group, an isooctyl group, a 2-ethylhexyl group, a n-nonyl group, an isononyl group, a n-decyl group, an isodecyl group, and a 2-propylheptyl group.

8. The plasticizer composition of claim 6, wherein, $R_{11}$ to $R_{15}$ are a 2-ethylhexyl group.

9. The plasticizer composition of claim 1, wherein:
the cyclohexane polyester-based substance is a compound of the following Chemical Formula 1-3; and
the perhydride comprises one or more compounds selected from the group consisting of compounds of the following Chemical Formulas 2-5 to 2-10:

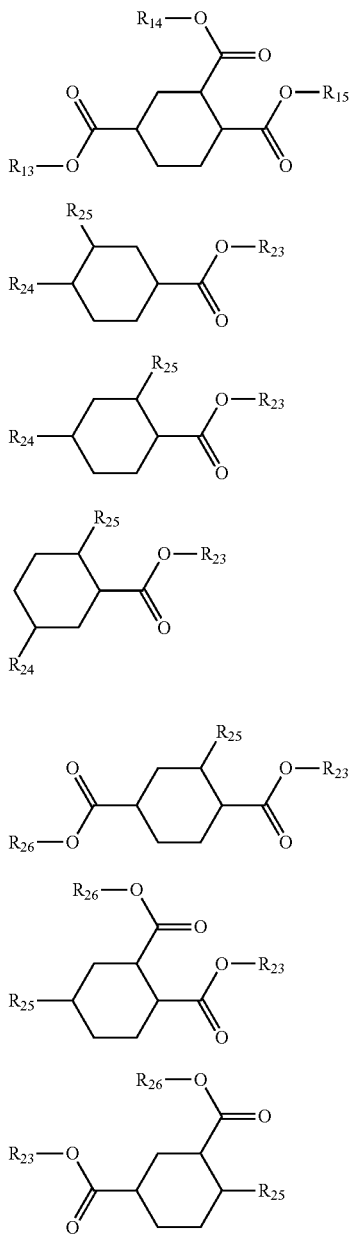

Chemical Formula 1-3

Chemical Formula 2-5

Chemical Formula 2-6

Chemical Formula 2-7

Chemical Formula 2-8

Chemical Formula 2-9

Chemical Formula 2-10 wherein:
$R_{13}$ to $R_{15}$ are each independently a C4 to C10 alkyl group;
$R_{23}$ and $R_{26}$ are each independently a C4 to C10 alkyl group; and
$R_{24}$ and $R_{25}$ are a methyl group.

10. The plasticizer composition of claim 9, wherein, $R_{13}$ to $R_{15}$, $R_{23}$ and $R_{26}$ are each independently selected from the group consisting of a n-butyl group, an isobutyl group, a n-pentyl group, an isopentyl group, a n-hexyl group, an isohexyl group, a n-heptyl group, an isoheptyl group, a n-octyl group, an isooctyl group, a 2-ethylhexyl group, a n-nonyl group, an isononyl group, a n-decyl group, an isodecyl group, and a 2-propylheptyl group.

11. The plasticizer composition of claim 9, wherein $R_{24}$ and $R_{25}$ are the methyl group.

12. The plasticizer composition of claim 1, wherein $R_{11}$ to $R_{15}$ and $R_2$ are each independently selected from the group consisting of a n-butyl group, an isobutyl group, a n-pentyl group, an isopentyl group, a n-hexyl group, an isohexyl group, a n-heptyl group, an isoheptyl group, a n-octyl group, an isooctyl group, a 2-ethylhexyl group, a n-nonyl group, an isononyl group, a n-decyl group, an isodecyl group, and a 2-propylheptyl group.

13. The plasticizer composition of claim 1, wherein $R_{11}$ to $R_{15}$ and $R_2$ are each independently selected from the group consisting of an isoheptyl group, a 2-ethylhexyl group, a n-nonyl group, an isononyl group, and a 2-propylheptyl group.

14. A method of preparing the plasticizer composition of claim 1, comprising:
hydrogenating any one aromatic carboxylic acid selected from the group consisting of isophthalic acid, terephthalic acid, and trimellitic acid to obtain a hydride including cyclohexanepolycarboxylic acid; and
esterifying the hydride with a primary alkyl alcohol, wherein:
the primary alkyl alcohol is a C4 to C10 alkyl alcohol; and
the cyclohexanepolycarboxylic acid is cyclohexane 1,3-dicarboxylic acid, cyclohexane 1,4-dicarboxylic acid, or cyclohexane 1,2,4-tricarboxylic acid.

15. A resin composition comprising:
a resin present in an amount of 100 parts by weight; and
the plasticizer composition of claim 1 present in an amount of 5 to 150 parts by weight.

16. The resin composition of claim 15, wherein the resin is one or more selected from the group consisting of ethylene-vinyl acetate, polyethylene, polypropylene, polyketone, polyvinyl chloride, polystyrene, polyurethane, natural rubber, synthetic rubber, and a thermoplastic elastomer.

* * * * *